United States Patent
Jolly et al.

(10) Patent No.: US 9,381,040 B2
(45) Date of Patent: Jul. 5, 2016

(54) COCHLEAR IMPLANT ELECTRODE INSERTION BRIDGE

(71) Applicant: MED-EL Elektromedizinische Geraete GmbH, Innsbruck (AT)

(72) Inventors: Claude Jolly, Innsbruck (AT); Anandhan Dhanasingh, Innsbruck (AT); Paul van de Heyning, Boom (BE)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 90 days.

(21) Appl. No.: 14/334,768

(22) Filed: Jul. 18, 2014

(65) Prior Publication Data

US 2015/0032123 A1   Jan. 29, 2015

Related U.S. Application Data

(60) Provisional application No. 61/858,655, filed on Jul. 26, 2013.

(51) Int. Cl.
*A61B 19/00* (2006.01)
*A61B 17/34* (2006.01)
*A61N 1/05* (2006.01)
*A61F 11/00* (2006.01)

(52) U.S. Cl.
CPC .......... *A61B 17/3468* (2013.01); *A61N 1/0541* (2013.01); *A61F 11/004* (2013.01)

(58) Field of Classification Search
CPC ............. A61N 1/0541; A61N 1/36032; A61B 17/3468; A61B 2017/00787; A61B 17/1679; A61B 2017/3488; A61B 2019/304; A61F 11/004; A61F 2002/183; A61F 2/18
USPC .................................................. 606/129, 137
See application file for complete search history.

(56) References Cited

U.S. PATENT DOCUMENTS

| 5,443,493 A | 8/1995 | Byers et al. |
|---|---|---|
| 6,397,110 B1 | 5/2002 | Kuzma |
| 6,408,855 B1 | 6/2002 | Berrang et al. |
| 2003/0069613 A1 | 4/2003 | Kuzma et al. |
| 2004/0243177 A1* | 12/2004 | Svehla et al. ................. 606/210 |
| 2004/0267359 A1* | 12/2004 | Makker et al. ............... 623/6.12 |
| 2006/0241723 A1* | 10/2006 | Dadd ................. A61B 17/3468 607/57 |
| 2009/0209972 A1 | 8/2009 | Loushin et al. |
| 2011/0319908 A1 | 12/2011 | Thenuwara et al. |

OTHER PUBLICATIONS

International Searching Authority, Authorized Officer Lee W. Young, International Search Report and Written Opinion—PCT/US14/47131, date of mailing Dec. 5, 2014, 16 pages.

* cited by examiner

*Primary Examiner* — Katherine M Shi
(74) *Attorney, Agent, or Firm* — Sunstein Kann Murphy & Timbers LLP

(57) ABSTRACT

An electrode guide bridge is used for inserting a cochlear implant electrode into a cochlea scala of a patient cochlea. An electrode holder encloses at least a portion of a cochlear implant electrode while allowing the electrode to slide freely without friction. A pointed distal tip of the electrode holder is sized to fit within a posterior tympanotomy during electrode insertion surgery and into an electrode opening in an outer surface of the patient cochlea without entering the cochlea scala to prevent an apical tip of the enclosed electrode from contacting tissues around the electrode opening during the insertion surgery.

6 Claims, 3 Drawing Sheets

COCHLEAR IMPLANT ELECTRODE INSERTION BRIDGE

This application claims priority from U.S. Provisional Patent Application 61/858,655, filed Jul. 26, 2013, which is incorporated herein by reference in its entirety.

FIELD OF THE INVENTION

The present invention relates to an insertion device for cochlear implant electrodes.

BACKGROUND ART

A normal ear transmits sounds as shown in FIG. 1 through the outer ear 101 to the tympanic membrane 102 which moves the bones of the middle ear 103 that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, auditory prostheses have been developed. For example, when the impairment is related to operation of the middle ear 103, a conventional hearing aid may be used to provide acoustic-mechanical stimulation to the auditory system in the form of amplified sound. Or when the impairment is associated with the cochlea 104, a cochlear implant with an implanted electrode can electrically stimulate auditory nerve tissue with small currents delivered by multiple electrode contacts distributed along the electrode.

FIG. 1 also shows some components of a typical cochlear implant system where an external microphone provides an audio signal input to an external signal processor 111 in which various signal processing schemes can be implemented. The processed signal is then converted into a digital data format for transmission by external transmitter coil 107 into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110. Typically, this electrode array 110 includes multiple stimulation contacts 112 on its surface that provide selective stimulation of the cochlea 104.

The electrode array 110 contains multiple electrode wires embedded in a soft silicone body referred to as the electrode carrier. The electrode array 110 needs to be mechanically robust, and yet flexible and of small size to be inserted into the cochlea 104. The material of the electrode array 110 needs to be soft and flexible in order to minimize trauma to neural structures of the cochlea 104. But an electrode array 110 that is too floppy tends to buckle too easily so that the electrode array 110 cannot be inserted into the cochlea 104 up to the desired insertion depth. A trade-off needs to be made between a certain stiffness of the electrode array 110 which allows insertion into the cochlea 104 up to the desired insertion depth without the array buckling, and certain flexibility of the electrode array 110 which keeps mechanical forces on the structures of the scala tympani of the cochlea 104 low enough.

One of the important steps in cochlear implant surgery is the insertion of the electrode array into the scala tympani of the cochlea. In some cases, this insertion process can be disrupted when the flexible tip of the electrode array 110 slips and sticks to the wet tissues around the electrode opening into the cochlea 104 rather than entering through the electrode opening as desired. This is frustrating and time consuming for the surgeon who often has to make repeated efforts to thread the tip of the electrode array 110 through the electrode opening. In addition, the contact with the wet tissues can deposit blood and other fluids onto the tip of the electrode array 110 which then contaminate the interior of the cochlea 104.

SUMMARY OF THE INVENTION

Embodiments of the present invention are directed to an electrode guide bridge and corresponding surgical method for inserting a cochlear implant electrode into a cochlea scala of a patient cochlea. An electrode holder encloses at least a portion of a cochlear implant electrode while allowing the electrode to slide freely without friction. A pointed distal tip of the electrode holder is sized to fit within a posterior tympanotomy during electrode insertion surgery and into an electrode opening in an outer surface of the patient cochlea without entering the cochlea scala to prevent an apical tip of the enclosed electrode from contacting tissues around the electrode opening during the insertion surgery.

The electrode holder is sized to fit within a mastoidectomy passage during the insertion surgery. There may be one or more enclosing wings that close over the enclosed portion of the electrode to prevent fluid entry. The electrode holder may be cylindrical. The distal tip may be harder than the electrode holder. The electrode opening may be a cochleostomy window or a surgical opening in the round window membrane of the patient cochlea.

DETAILED DESCRIPTION OF SPECIFIC EMBODIMENTS

Embodiments of the present invention are based on using an electrode guide bridge that is placed in the posterior tympanotomy with a pointed distal tip that fits within the electrode opening in the cochlea—e.g., a round window opening or cochleostomy. The cochlear implant electrode fits within the guide bridge and slides through it, over the distal tip to reach the electrode opening without touching the surrounding tissue where it would get stuck and contaminated.

Figure 1:
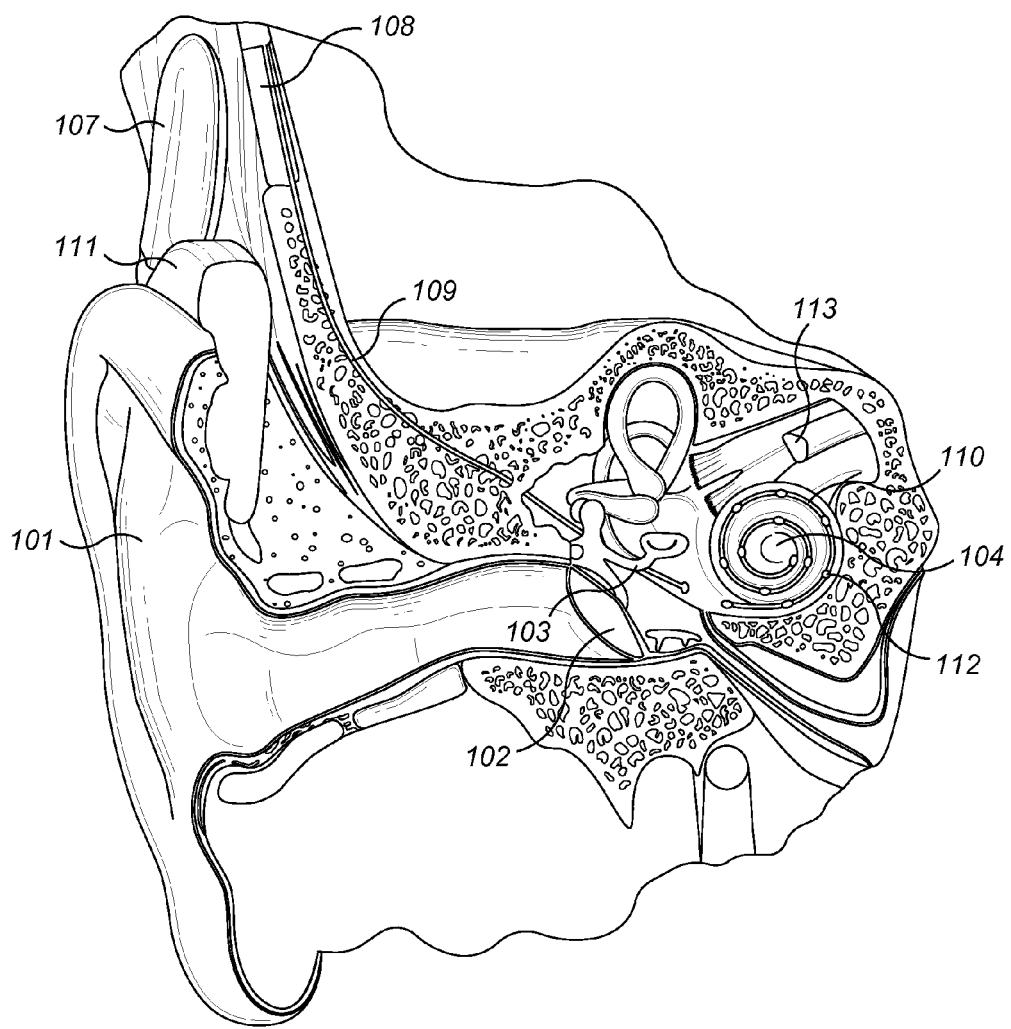
FIG. 1 shows the anatomy of the human ear with a cochlear implant system.
Figure 2:
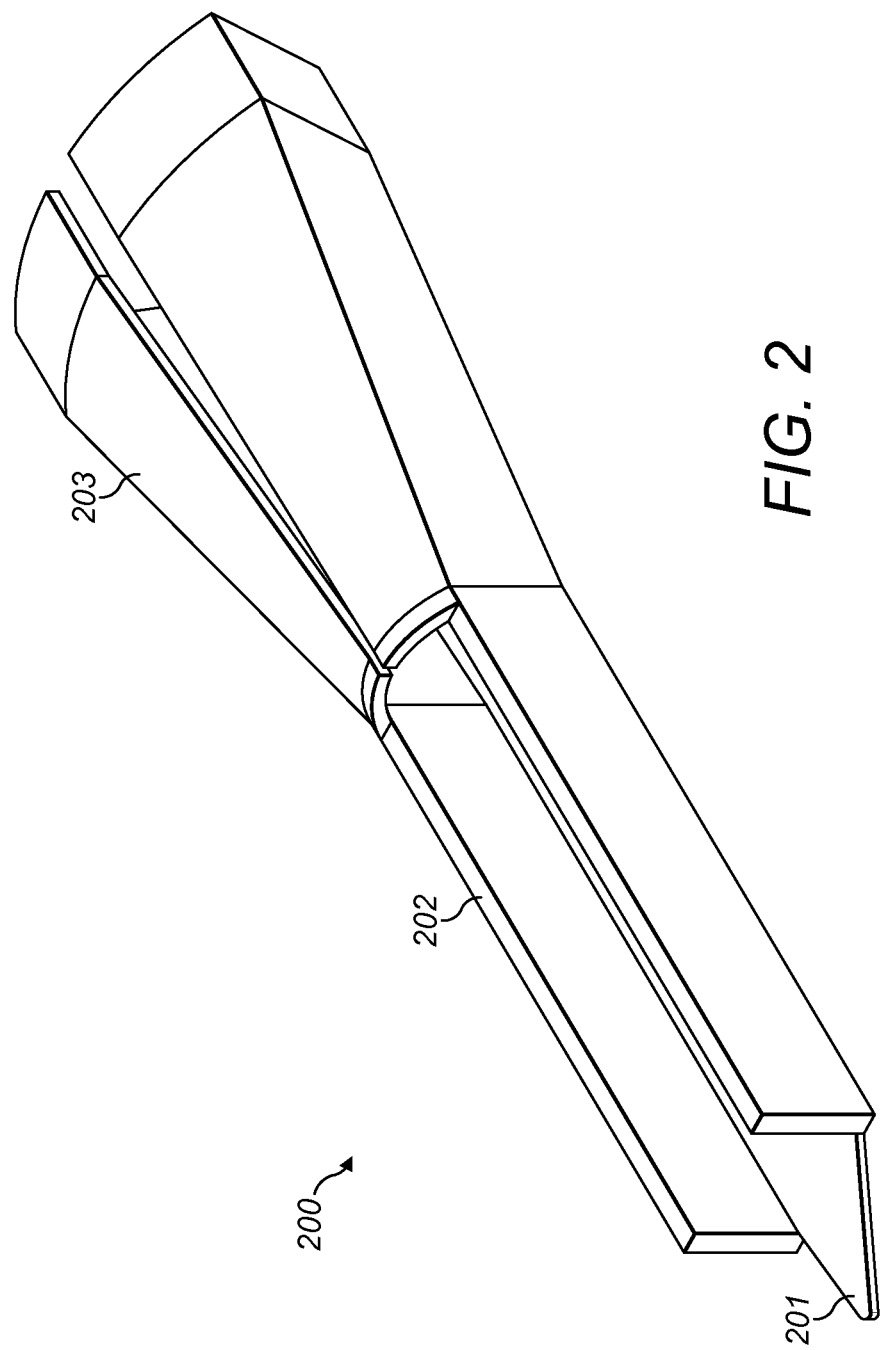
FIG. 2 shows an example of an electrode guide bridge according to one embodiment of the present invention.
Figure 3:
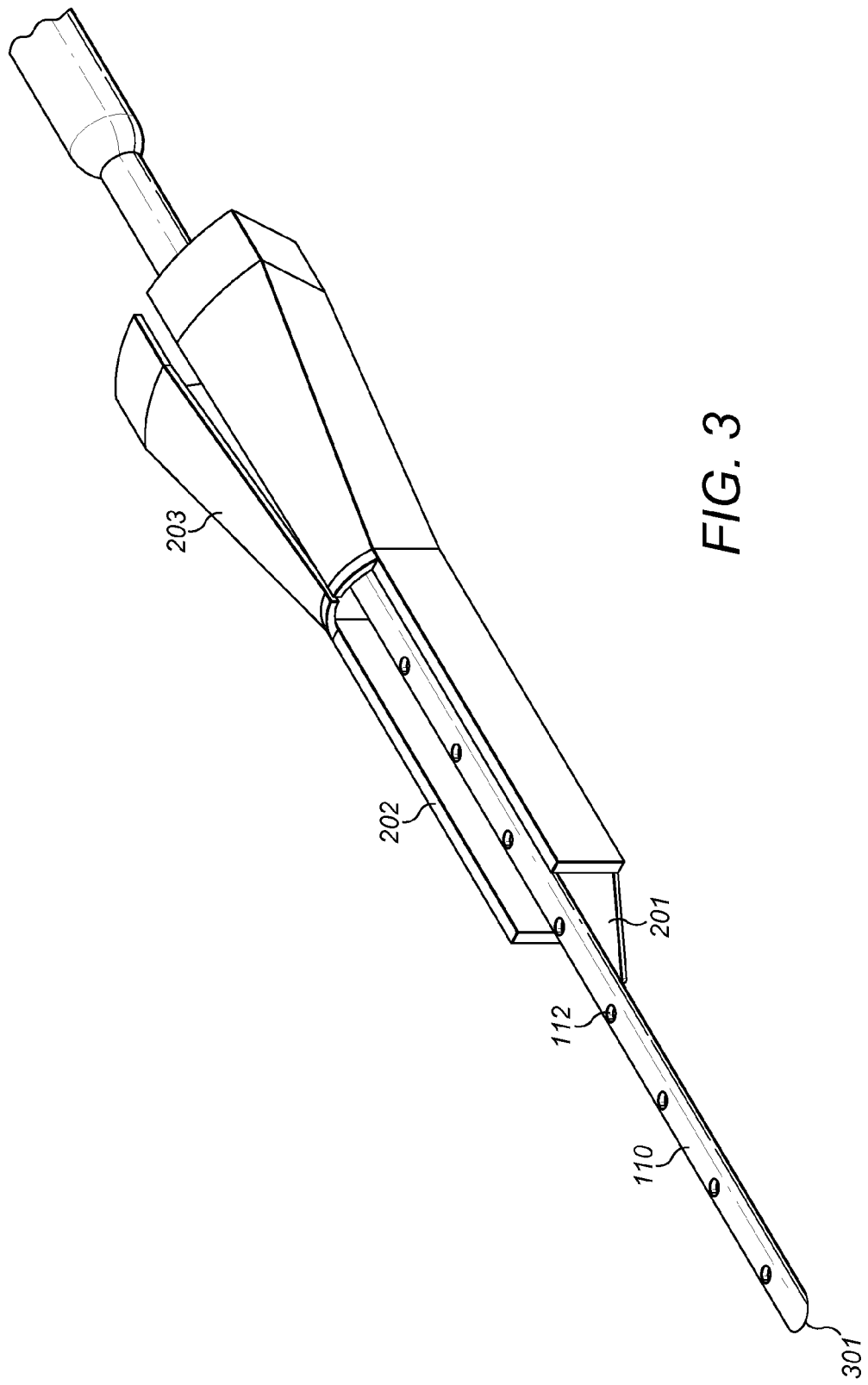
FIG. 3 shows an electrode guide bridge holding a cochlear implant electrode for surgical insertion.

FIG. 2 shows an example of an electrode guide bridge 200 according to one embodiment of the present invention, and FIG. 3 shows such an electrode guide bridge 200 holding a cochlear implant electrode 110 for surgical insertion. An electrode holder 202 portion of the guide bridge 200 encloses at least a portion of the cochlear implant electrode 110 while allowing it to slide within freely without friction. The electrode holder 202 may be made of any biocompatible material (e.g., plastic) and is sized to fit within a mastoidectomy passage during the insertion surgery. In the embodiment shown, the electrode holder 202 includes enclosing wings 203 that close over at least part of the enclosed portion of the electrode 110 (e.g., the portion that fits in the mastoidectomy passage) to prevent fluid entry and contamination of the enclosed electrode 110. The electrode holder 202 may be any convenient shape, for example, cylindrical.

A pointed distal tip 201 of the electrode holder 202 is sized to fit within the posterior tympanotomy during electrode insertion surgery and into an electrode opening (e.g., cochleostomy or round window opening) in an outer surface of the patient cochlea without entering the cochlea scala. Typically the distal tip 201 may be made of a harder material (e.g., a harder plastic) than the rest of the electrode holder 202. Together the electrode holder 202 and the distal tip 201 prevent an apical tip of the enclosed electrode 110 from contacting tissues around the electrode opening during the insertion surgery.

Although various exemplary embodiments of the invention have been disclosed, it should be apparent to those skilled in the art that various changes and modifications can be made which will achieve some of the advantages of the invention without departing from the true scope of the invention.

What is claimed is:

1. An electrode guide bridge for inserting a cochlear implant electrode into a cochlea scala of a patient cochlea, the guide bridge comprising:

an electrode holder comprising a body portion and a pointed distal tip portion harder than the body portion, wherein the body portion encloses at least a portion of a cochlear implant electrode while allowing the electrode to slide freely without friction; and the pointed distal tip portion of the electrode holder being configured to fit within a posterior tympanotomy during electrode insertion surgery and into an electrode opening in an outer surface of the patient cochlea without entering the cochlea scala to prevent an apical tip of the enclosed electrode from contacting tissues around the electrode opening during the insertion surgery.

2. An electrode guide bridge according to claim 1, wherein the electrode holder is sized to fit within a mastoidectomy passage during the insertion surgery.

3. An electrode guide bridge according to claim 1, wherein the electrode holder includes one or more enclosing wings that close over the enclosed portion of the electrode to prevent fluid entry.

4. An electrode guide bridge according to claim 1, wherein the electrode holder is cylindrical.

5. An electrode guide bridge according to claim 1, wherein the electrode opening is a cochleostomy window in the outer surface of the patient cochlea.

6. An electrode guide bridge according to claim 1, wherein the electrode opening is a surgical opening in the round window membrane of the patient cochlea.

\* \* \* \* \*